United States Patent
Byström et al.

(10) Patent No.: US 12,274,991 B2
(45) Date of Patent: Apr. 15, 2025

(54) REACTOR ARRANGEMENT COMPRISING A MEANS FOR ROTATING AND/OR OSCILLATING A TRANSFORMATION DEVICE AND A METHOD OF USING SUCH REACTOR ARRANGEMENT

(71) Applicant: Spinchem AB, Umeå (SE)

(72) Inventors: Emil Byström, Tavelsjö (SE); Erik Löfgren, Umeå (SE); Alexander Berggren, Umeå (SE)

(73) Assignee: Spinchem AB, Umeå (SE)

( * ) Notice: Subject to any disclaimer, the term of this patent is extended or adjusted under 35 U.S.C. 154(b) by 481 days.

(21) Appl. No.: 17/753,857

(22) PCT Filed: Aug. 25, 2020

(86) PCT No.: PCT/EP2020/073720
§ 371 (c)(1),
(2) Date: Mar. 16, 2022

(87) PCT Pub. No.: WO2021/052724
PCT Pub. Date: Mar. 25, 2021

(65) Prior Publication Data
US 2022/0331759 A1   Oct. 20, 2022

(30) Foreign Application Priority Data
Sep. 18, 2019 (SE) .................... 1951055-1

(51) Int. Cl.
*B01F 27/94* (2022.01)
*B01F 27/81* (2022.01)
(Continued)

(52) U.S. Cl.
CPC ............ *B01F 27/941* (2022.01); *B01F 27/81* (2022.01); *B01F 31/449* (2022.01); *B01J 8/10* (2013.01);
(Continued)

(58) Field of Classification Search
CPC ...... B01F 27/941; B01F 27/81; B01F 31/449; B01F 2101/2204; B01F 2101/305;
(Continued)

(56) References Cited

U.S. PATENT DOCUMENTS 2,712,229 A   7/1955 Jones
4,683,062 A * 7/1987 Krovak .................. B01J 8/10
                                                 210/150
(Continued)

FOREIGN PATENT DOCUMENTS

EP    3 107 651 A1   12/2016
EP    3 445 482 A1   2/2019
WO    2014020976 A1  2/2014

OTHER PUBLICATIONS

International Search Report and Written Opinion mailed Jan. 18, 2021, issued in corresponding International Patent Application No. PCT/EP2020/073720, filed Aug. 25, 2020, 10 pages.
(Continued)

*Primary Examiner* — Madeline Gonzalez
(74) *Attorney, Agent, or Firm* — Christensen O'Connor Johnson Kindness PLLC

(57) ABSTRACT

A reactor arrangement for performing, by means of at least one solid reaction member(s), a biological or chemical transformation, or physical or chemical trapping from, or release of agents to, a fluidic media in a continuous process. The arrangement comprises at least one reactor with a cylindrical reaction vessel (11) in which at least one reactor a transformation device (100) has been mounted. The vessel (11) comprises at least one inlet port (30) in the vicinity of its bottom wall (18) and at least one outlet port (40) arranged in the vicinity of its upper end portion. Each inlet port (30) is connected to a fluid supply member (300) configured to be submerged below the fluid surface level in a pool or a pond. The fluid supply member (300) comprises at least one inlet
(Continued)

Figure 1:
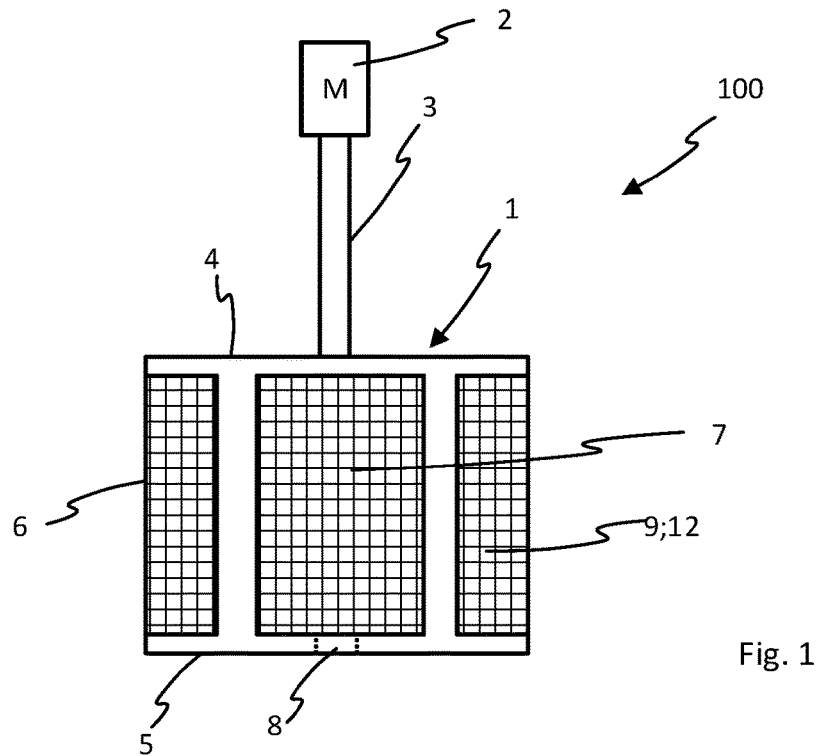

opening (301) configured to continuously supply a fluid from the pool or the pond to the vessel (11). Each outlet port (40) is configured to continuously let out the fluid from the vessel (11) to the pool or the pond via the outlet port (40). Further a method of using the reactor arrangement is provided.

13 Claims, 6 Drawing Sheets

(51) Int. Cl.

| | | |
|---|---|---|
| *B01F 31/44* | (2022.01) | |
| *B01J 8/10* | (2006.01) | |
| *B01J 19/18* | (2006.01) | |
| *B01J 19/28* | (2006.01) | |
| *C02F 1/28* | (2023.01) | |
| *C02F 1/68* | (2023.01) | |
| *C02F 3/00* | (2023.01) | |
| *C12M 3/04* | (2006.01) | |
| *G21F 9/12* | (2006.01) | |
| *G21F 9/18* | (2006.01) | |
| *B01F 101/00* | (2022.01) | |
| *B01F 101/44* | (2022.01) | |

(52) U.S. Cl.
CPC .......... *B01J 19/1806* (2013.01); *B01J 19/28* (2013.01); *C02F 1/28* (2013.01); *C02F 1/688* (2013.01); *C02F 3/00* (2013.01); *C12M 27/10* (2013.01); *G21F 9/12* (2013.01); *G21F 9/18* (2013.01); *B01F 2101/2204* (2022.01); *B01F 2101/305* (2022.01); *B01F 2101/44* (2022.01); *B01J 2208/00867* (2013.01); *B01J 2208/00876* (2013.01); *C02F 2201/002* (2013.01)

(58) Field of Classification Search
CPC ......... B01F 2101/44; B01F 27/94; B01J 8/10; B01J 19/1806; B01J 19/28; B01J 2208/00867; B01J 2208/00876; B01J 2208/00814; C02F 1/28; C02F 1/688; C02F 3/00; C02F 2201/002; C02F 2101/006; C02F 2103/002; C02F 2103/007; C02F 2103/06; C02F 2103/08; C02F 2201/008; C02F 2209/008; C02F 1/001; C02F 2301/024; C12M 27/10; G21F 9/12; G21F 9/18
USPC ...... 210/601, 167.01, 167.1, 167.13, 167.15, 210/167.17, 170.02, 170.09, 172.4, 172.6, 210/174, 194, 205, 210, 211, 212, 213, 210/217, 220, 359, 360.1, 365, 367, 210/380.1, 256
See application file for complete search history.

(56) References Cited

U.S. PATENT DOCUMENTS

2014/0177379 A1   6/2014   Hattori
2019/0118151 A1   4/2019   Byström et al.

OTHER PUBLICATIONS

Swedish Search Report mailed Apr. 20, 2020, issued in corresponding Swedish Application No. 1951055-1, filed.Sep. 18, 2019, 2 pages.

* cited by examiner

REACTOR ARRANGEMENT COMPRISING A MEANS FOR ROTATING AND/OR OSCILLATING A TRANSFORMATION DEVICE AND A METHOD OF USING SUCH REACTOR ARRANGEMENT

FIELD OF INVENTION

The present invention relates to a reactor arrangement and a method of using such reactor arrangement.

BACKGROUND OF THE INVENTION

One common way of storing contaminated subject matter, and especially radioactive waste material, is to store it submerged in a pool or pond. Submersion in a fluid is also used in active nuclear plants to shield radioactivity radiating from the nuclear material and parts of the plant associated with the nuclear material. The fluid in the pool or pond will act as a shield that restricts the radioactivity from being spread into the ambient atmosphere. However, over time, the radioactivity in the fluid will gradually increase and the shielding action will be impaired.

From a medical point of view there are limitations in view of the amount of radioactivity that operative personnel may be subjected to during a certain time limit. This has implications on the operative work in this kind of environment. Not only is it time consuming in terms of dressing and undressing protective clothing when entering/leaving the premises, but it is also labour intensive since more people must be involved to provide necessary man hours.

There are also other environments where there is a need for processing large volumes of fluid. This may by way of example be in natural ponds to control pH or to take care of bleeding-off or discharge of contaminating substances. Other examples are treatment of leachate in mining districts or treatment of greywater.

There is hence a need for technology that allows processing of large volumes of fluid in pools or ponds, which processing may be performed continuously and remotely with a limited involvement of human presence. The technology should be capable of being operated in remote areas, across large areas and for continuous processing of large fluid volumes.

SUMMARY OF THE INVENTION

According to a first aspect, the invention provides reactor arrangement for performing, by means of at least one solid reaction member(s), a biological or chemical transformation, or physical or chemical trapping from, or release of agents to, a fluidic media in a continuous process, wherein said reactor arrangement comprises at least one reactor, wherein said at least one reactor comprises a cylindrical reaction vessel in which at least one reactor a transformation device has been mounted, said cylindrical reaction vessel comprising a bottom wall and a cylindrical side wall extending from the bottom wall; and wherein said transformation device comprises:

a flow distributor having an essentially cylindrical shape, a first essentially flat surface, a second essentially flat surface, and a peripheral wall having an essentially circular cross-section, at least one fluid medium inlet located in vicinity of the center of said first and/or second surface, said inlet being adapted for receiving fluid medium and optionally being adapted for receiving initially suspended solid reaction members, at least one fluid medium outlet permeable for said fluid medium but impermeable for solid reaction members, said outlet(s) being located on said peripheral wall, a driving shaft located on said first surface for enabling rotation or oscillation of the flow distributor, and at least one confinement wherein said solid reaction member(s) can be trapped and said transformation is performed; and a means for rotating and/or oscillating the transformation device; and wherein the said cylindrical reaction vessel comprises:

at least one inlet port arranged in the vicinity of the bottom wall and at least one outlet port arranged in the vicinity of an upper end portion of the cylindrical reaction vessel, and wherein each of the at least one inlet port is connected to a fluid supply member configured to be submerged below the fluid surface level in a pool or a pond, said fluid supply member having at least one inlet opening configured to continuously supply a fluid from the pool or the pond to the cylindrical reaction vessel via said at least one inlet port, and each of the at least one outlet port is configured to continuously let out the fluid from the vessel to the pool or the pond via the at least one outlet port.

Accordingly, a reactor arrangement is provided that allows continuous processing of large fluid volumes, by means of at least one solid reaction member(s), a biological or chemical transformation, or physical or chemical trapping from, or release of agents to, a fluidic media. The process may be run in e.g. a pond or a pool to process the fluid contained therein.

In the context of the invention, the term "pond" should be understood as a natural/artificial water reservoir having a non-restricted and changeable surface extension/depth. A pond may by way of example be a lake, a dam, a ditch, a creek or even a bay. The fluid must not be still.

In the context of the invention, the term "pool" should be understood as an indoor/outdoor artificial water reservoir with a defined area and depth.

The provided reactor arrangement uses a rotating transformation device, that as a result of a high-speed rotation thereof generates a vortex inside the vessel that is strong enough to cause a suction action that sucks fluid to be processed from the pond or pool, into the vessel via the at least one opening in the fluid supply member and the inlet port of the vessel. The fluid to be processed is not only sucked into the vessel as such by the vortex but also sucked, by a circulating flow, into the confinement of the transformation device via it's at least one fluid medium inlet. From there, the fluid is forced in the radial direction to leave the confinement via the peripheral fluid permeable wall. The circulating flow in and out of the confinement will cause a dwell time of the fluid in the vessel and in the confinement, whereby the fluid is allowed to react with the at least one solid reaction member contained in the confinement. Accordingly, the fluid which is continuously supplied to the vessel is continuously processed inside the transformation device while being in contact with the solid reaction members contained therein.

It goes without saying that the continuous suction action will fill the vessel with fluid and as a result thereof the surplus fluid which has been processed will inherently be forced to leave the vessel via the at least one outlet port and be released by being returned to the pool or pond.

Even though the dwell time in the reaction vessel should not be sufficient to reach a complete chemical reaction, the dwell time will be sufficient to at least have initiated a chemical reaction which as such will render the released processed fluid to be of a higher quality than the non-processed fluid that is sucked into the vessel. In the context of the invention, the term "higher quality" should be understood as that the processed fluid has undergone a certain degree of chemical reaction or purification, which reaction or purification as such must not be completed. Rather, the quality should be higher than the overall quality in the pond or pool. Depending on the type of process to be run, the quality could be determined, by way of non-limited examples as a reduced radioactivity, a reduced or increased pH, or a reduced or increased amount of a specific chemical compounds or agent.

The skilled person will understand that the solid reaction members after a certain time will be consumed. The hence used solid reaction members may be replaced and the process continued anew. Alternatively, the complete transformation device may be disposed and replaced by a new transformation device filled with fresh solid reaction members. The latter is especially the case in the event the reactor arrangement is arranged in a radioactive environment.

It is to be understood that the released processed fluid will initially have a locally high concentration as measured in and around the outlet port before gradually being dissolved in the overall volume of the pool or pond. In terms of the pond or pool containing a radioactive fluid, the released processed fluid will have a shielding effect as seen in the vertical direction which prevents radioactivity from spreading in the atmosphere. The shielding action may also be applicable in other environments to restrict spreading of gaseous subject matter into the ambience.

The reactor arrangement in line with the invention has been successfully tried for reduction of activity level of radioactive species. By way of example, Cs-Treat media being a granular hexacyanoferrate manufactured by Fortum, Finland may be used to selectively remove Cs-137 from liquid wastes. Another material, Radex Sb-1000 from Graver Technologies, may be used for the treatment of nuclear liquid radwaste. It is uniquely designed to reduce the activity level of radioactive species and is especially effective for the reduction of Antimony-125 (125Sb).

The fluid supply member may be an elongated hose or tube comprising multiple inlet openings arranged along the longitudinal extension thereof, a grid system with an array of hoses or tubes comprising multiple inlet openings, a combination of one or more of an elongated hose, a tube or a grid, each of them comprising multiple inlet openings, or a plurality of arms in the form of tubes or hoses branching from a common supply pipe, said arms comprising multiple inlet openings arranged along their longitudinal extensions.

By using a hose, a tube or a grid provided with multiple inlet openings, a large area of the pond or pool may be covered by one and the same reactor arrangement. Further, by using multiple inlet openings, the functionality of the arrangement may be maintained although one or more inlet openings should be blocked over time by e.g. deposits or sludge. The inlet openings may be provided as a plurality of perforations.

In case of the fluid supply member being a hose, this is preferably flexible.

In case of the fluid supply member being a grid-system, this preferably comprises a design which may be handled as one single unit during submerging and elevation.

The cylindrical reaction vessel may, during operation of the transformation device, be configured to be arranged above the fluid surface level in a pool or in a pond supported by a scaffold or by a floating platform; or the cylindrical reaction vessel may, during operation of the transformation device, be configured to be submerged in a pool or in a pond, while the at least one inlet opening of the fluid supply member is arranged to be submerged below the fluid surface level in said pool or pond at a position remote from the at least one outlet port of the cylindrical reaction vessel.

In the context of the invention, the term "remote" should be understood as a distance large enough for a fluid volume at a first location not to be affected by any vortex or turbulence caused by an activity caused by the operation of the reactor arrangement at another location. Especially, any turbulence created in or around the at least one inlet opening of the fluid supply member during operation of the transformation device, should not influence the fluid in the area in and around the at least one outlet port of the cylindrical reaction vessel. As the processed fluid is continuously released from the vessel it will form a virtual fluid volume in the pool which initially has a virtual cross section as seen in a horizontal plane. This virtual fluid volume will act as a shielding in view of the underlying volume in the pool. It is to be understood that in the long run, a general dissolution will occur due to natural movements in the overall fluid volume in the pool or pond, however, the longer the dissolution may be delayed by a remote distance between the at least one inlet opening of the fluid supply member and the at least one outlet port of the reaction vessel, the better shielding action may be provided for. As a practical example, in terms of the pond or pool containing a radioactive fluid, the released processed fluid will have a shielding effect as seen in the vertical direction which prevents radioactivity from spreading in the atmosphere. The reduced radioactivity in the air above surface level will allow an improved better working environment for personnel in the area around the pool.

The use of a scaffold may be suitable in the event of a pool, since the area of a pool typically is defined by rigid side walls and thereby has a well-defined area. The scaffold may in such case be a permanent installation supported by the walls of the pool or be suspended in a ceiling above the pool. The scaffold may be provided with a traverse crane allowing the reaction vessel to be moved across the pool area.

Alternatively, the cylindrical reaction vessel may be supported by a floating platform. The floating platform may be a movable platform that may be anchored at a specific position in the pool or the pond. Alternatively, the floating platform may be a remotely controlled vehicle or an autonomous vehicle. The floating platform may be connected to a GPS system allowing a precise positioning.

Alternatively, the cylindrical reaction vessel may, during operation of the transformation device, be configured to be submerged in a pool or in a pond, while the at least one inlet opening of the fluid supply member is arranged to be submerged below the fluid surface level in said pool or pond at a position remote from the cylindrical reaction vessel.

In other words, the cylindrical reaction vessel containing the transformation device may be arranged above the fluid level, be submerged below fluid level, or even be partially submerged. Thus, the at least one outlet port may be arranged above surface level.

The at least one outlet port may be formed by an open mouth of the cylindrical reaction vessel opposite the bottom wall; or by at least one through going opening in the cylindrical side wall.

In an embodiment where the outlet port is formed by an open mouth of the cylindrical reaction vessel, the processed fluid may be allowed to be released by flooding the edge which delimits said mouth. This is applicable no matter if the cylindrical reaction vessel is completely or partially submerged below surface level, supported on a scaffold or by a floating platform.

The cylindrical reaction vessel may further comprise a top wall formed as a removable lid, and wherein the at least one outlet port is arranged in said top wall.

Each of the at least one outlet ports may be connected to a fluid distribution member having at least one outlet opening, and the fluid distribution member, may during operation of the transformation device be configured to be arranged above the fluid surface in a pool or in a pond; be arranged floating on the fluid surface in a pool or in a pond; or be configured to be submerged below the fluid surface level in said pool or pond in a position remote from the cylindrical reaction vessel and/or from the at least one inlet opening of the fluid supply member.

A fluid distribution member connected to the at least one outlet port may be provided to ensure a large distance between the outlet of the processed fluid and the cylindrical reaction vessel and/or the at least one inlet opening of the fluid supply member. Thereby the risk of undue disturbance of the released flow of processed fluid may be minimized. This may delay dissolving of the processed fluid into the non-processed fluid and hence prolong a shielding effect.

Further, a fluid distribution member may be used to distribute the processed fluid across an enlarged area. The fluid distribution member may in its easiest form be a free, open end of a hose or tube. In other embodiments, the fluid distribution member may be of the same type as the fluid supply member, i.e. an elongated hose or tube comprising multiple outlet openings arranged along the longitudinal extension thereof, a grid system with an array of hoses or tubes comprising multiple outlet openings, or a combination of one or more of an elongated hose, a tube or a grid, each of them comprising multiple outlet openings. The fluid distribution member may also be a plurality of arms in the form of tubes or hoses branching from a common supply pipe, said arms comprising multiple inlet openings arranged along their longitudinal extensions An inner surface of the cylindrical reactor vessel may comprise means for enhancing fluidic shear stress in any of two rotary directions of the transformation device. As disclosed herein, the term "means for enhancing the fluidic shear stress" relates to some type of protrusions from the inner surface capable of causing perturbations in the fluidic media flow close to the inner wall of the reactor vessel that is caused by the rotational movement of the flow distributor. The means for enhancing fluidic shear stress may by way of example be one or more baffles. The baffles may be integrated in the inner surface of the vessel or be arranged as an insert.

The cylindrical reactor vessel may further comprise at least one opening which optionally may be fitted with a member for remote exchange of transformation matter or for receiving a measurement probe. The measurement probes may be connected to a control computer to allow an analysis and better control of the conditions prevailing in the cylindrical reaction vessel and hence the continuous process. Examples of measurement probes are thermometric or photometric sensor probes, and various electrodes for carrying out electrochemical measurements.

The at least one reactor may comprise a pump configured to enhance the flow of fluid from the at least one inlet opening of the fluid supply member, into the vessel and out of the vessel via said at least one outlet opening of the fluid distribution member, thereby assisting inherent pumping action of the transformation device during rotation and/or oscillating of the transformation device. The pump may be arranged in any suitable position between the different components of the arrangement. The pump may be arranged either above or below the surface level.

The reactor may comprise an agitator for stirring said fluidic media. The agitator may be assisted by a plurality of baffles.

According to another aspect, a method for performing, by means of at least one solid reaction member(s), a biological or chemical transformation, or physical or chemical trapping from, or release of agents to, a fluidic media in a continuous process, wherein said reactor arrangement comprises at least one reactor. The method comprises the acts of:
  a) providing a reactor arrangement according to any of claims 1-8;
  b) adding at least one solid reaction member to a confinement of said flow distributor;
  c) submerging the fluid supply member and its at least one inlet opening below the fluid surface level in a pool or in a pond, thereby allowing fluid to be supplied from the pool or pond to the cylindrical reaction vessel via the at least one inlet opening;
  d) arranging the cylindrical reaction vessel with its at least one outlet port at a position remote from the at least one inlet opening of the fluid supply member, said remote position being arranged on a distance from the at least one inlet opening so that any turbulence created in or around the at least one inlet opening of the fluid supply member during operation of the transformation device, does not influence the fluid in the area in and around the at least one outlet port of the cylindrical reaction vessel; and
  e) activating the means for rotating and/or oscillating the transformation device, whereby the biological or chemical transformation, or physical or chemical trapping from, or release of agents to, the fluidic media is initiated and continuously run.

The reactor arrangement and its operation and advantages has been thoroughly discussed above. Those arguments are equally applicable to the method of performing a process by using such reactor. Thereby, in order to avoid undue repetition, reference is made to the sections above.

The cylindrical reaction vessel containing the transformation device may be arranged above the fluid surface level in a pool or in a pond supported by a scaffold or by a floating platform; or the cylindrical reaction vessel may be arranged submerged in a pool or in a pond.

The at least one outlet port of the cylindrical reaction vessel may be an open mouth of the vessel opposite the bottom wall, whereby the processed fluid is continuously let out from the vessel to the pool or pond by flooding an edge portion of the vessel delimiting said open mouth during rotation or oscillation of the transformation device.

At least one outlet port of the cylindrical reaction vessel may be connected to a fluid distribution member having at least one outlet opening, whereby the processed fluid is continuously let out from the vessel to the pool or pond via the at least one outlet opening of the fluid distribution member during rotation or oscillation of the transformation device.

The fluidic media may be a radioactive fluid, sea water, lake water, leachate or greywater.

BRIEF DESCRIPTION OF THE ENCLOSED FIGURES

The present invention will now be further disclosed with reference to the enclosed figures, in which:

FIG. 1 discloses one embodiment of a transformation device.

Figure 2:
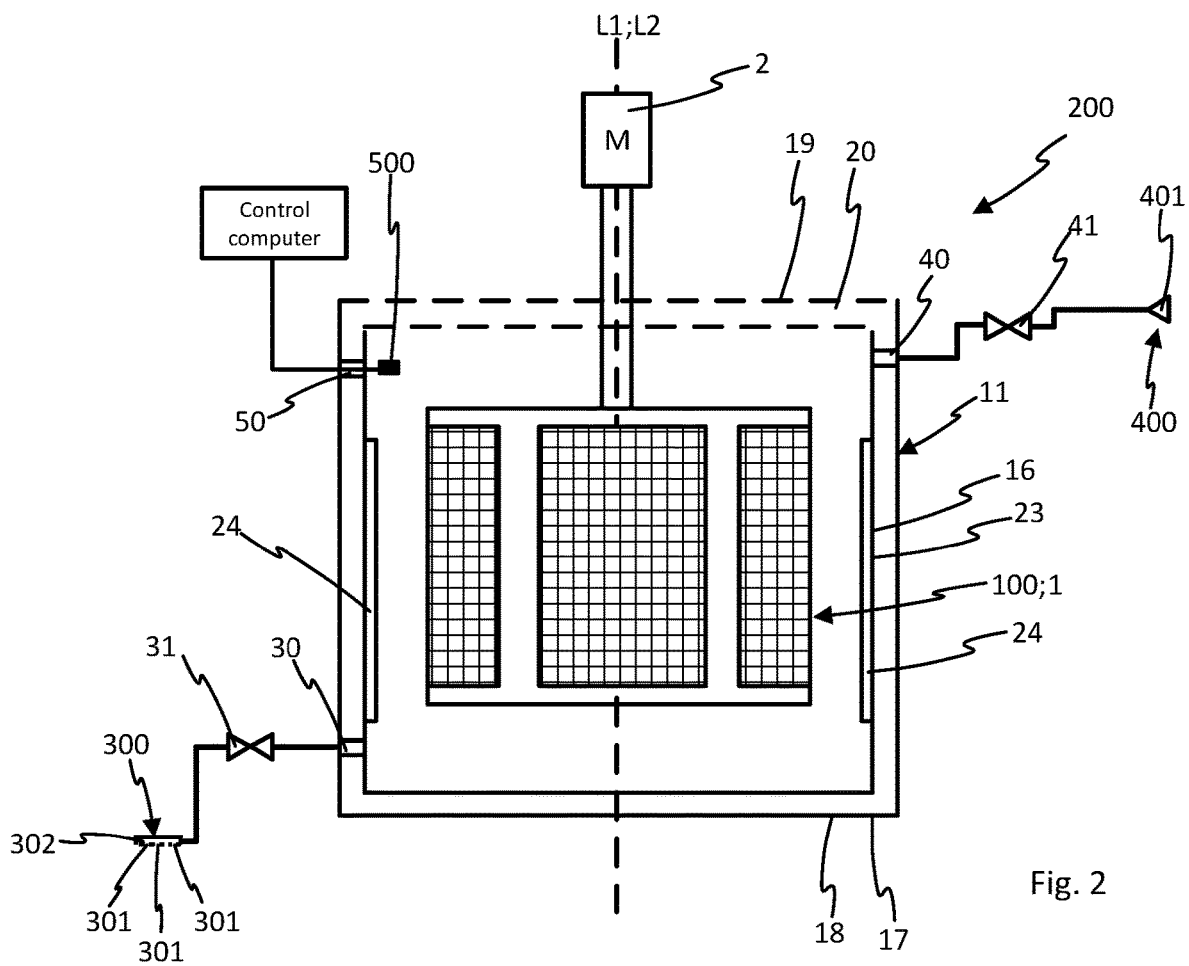

FIG. 2 discloses a reactor with an implemented flow distributor.

Figure 3A:
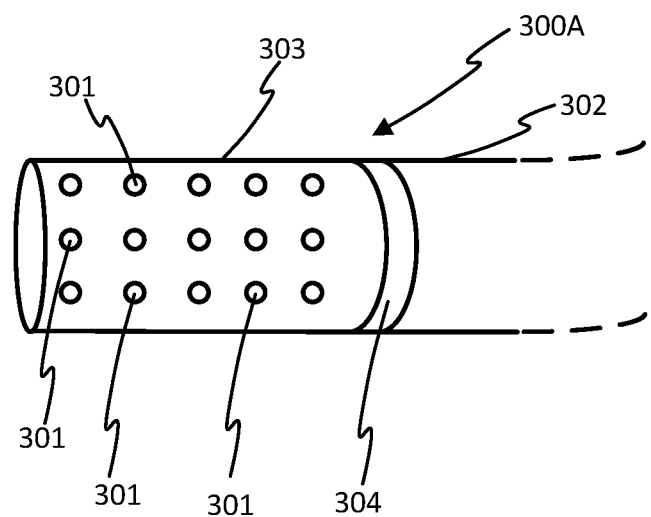
Figure 3B:
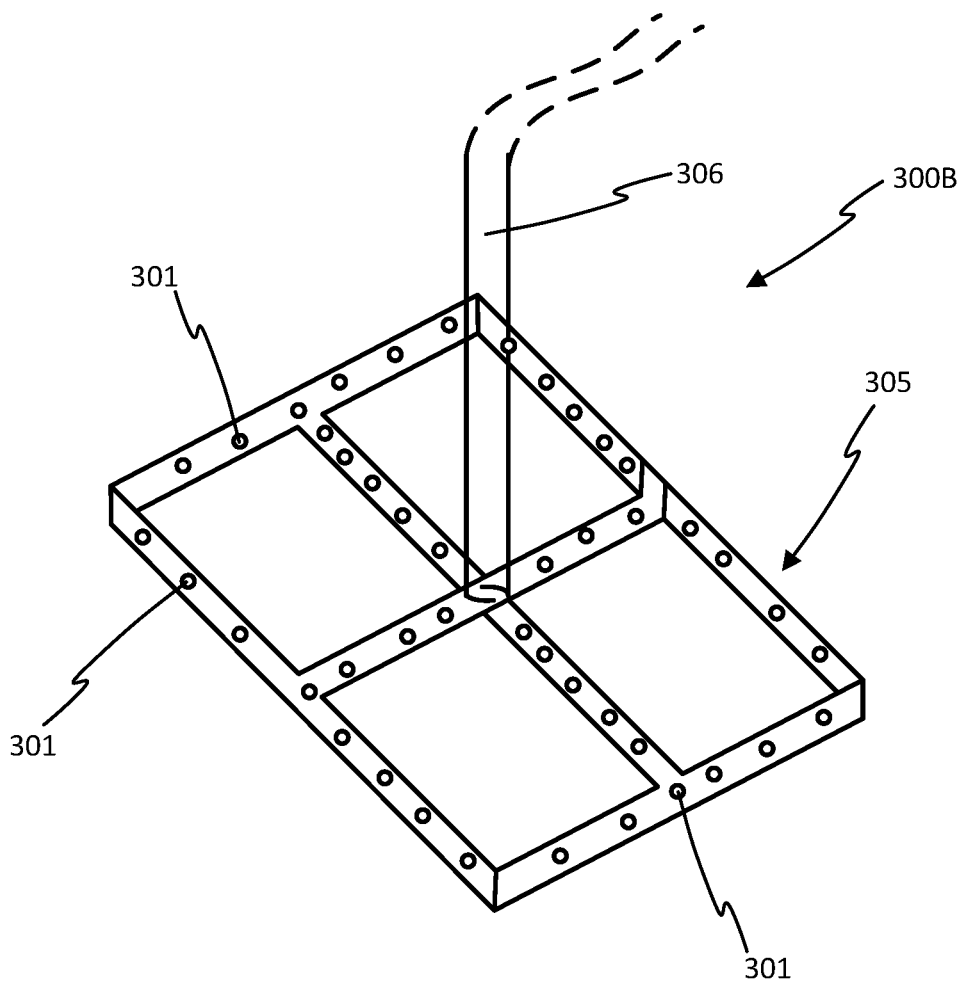
Figure 3C:
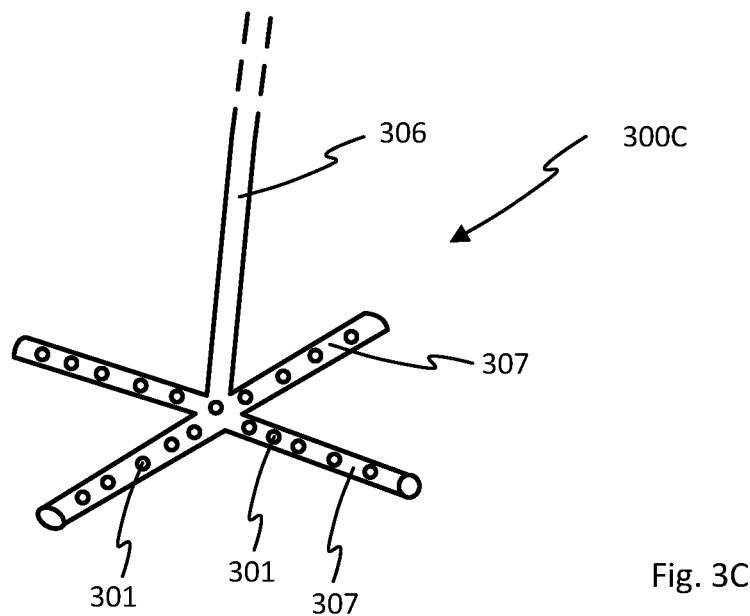

FIGS. 3A-3C disclose different embodiments of a fluid supply member.

Figure 4:
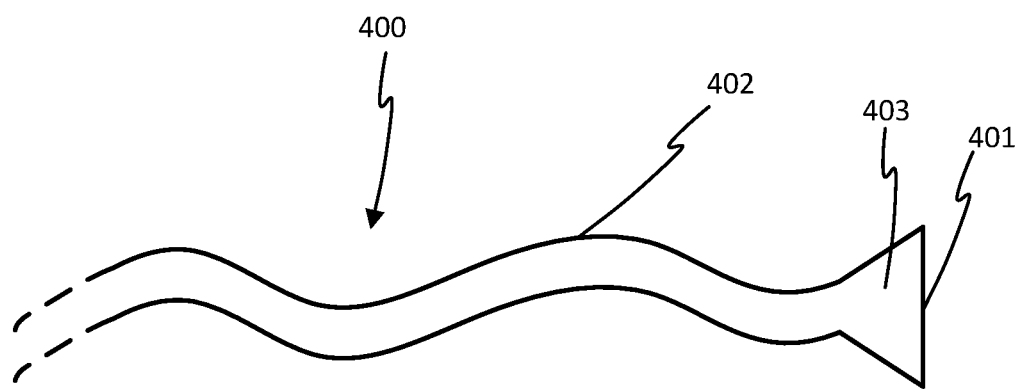

FIG. 4 discloses one embodiment of a fluid distribution member.

Figure 5:
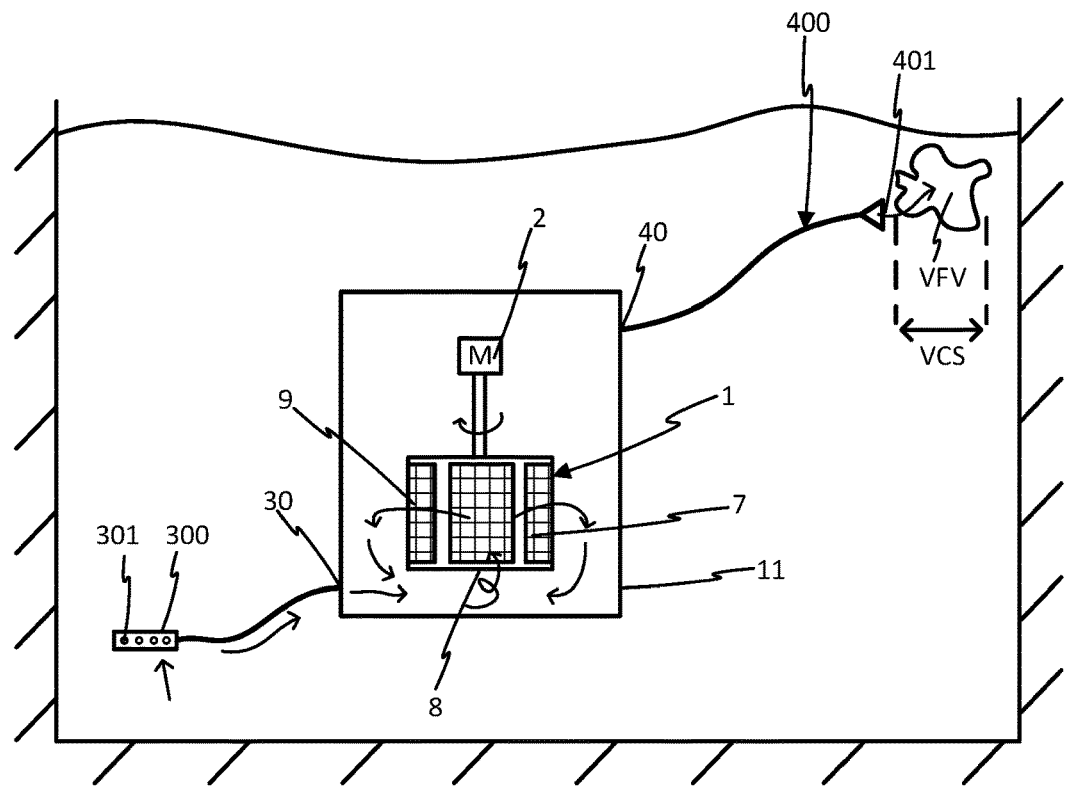

FIG. 5 discloses a first example of the operation of the reactor arrangement.

Figure 6:
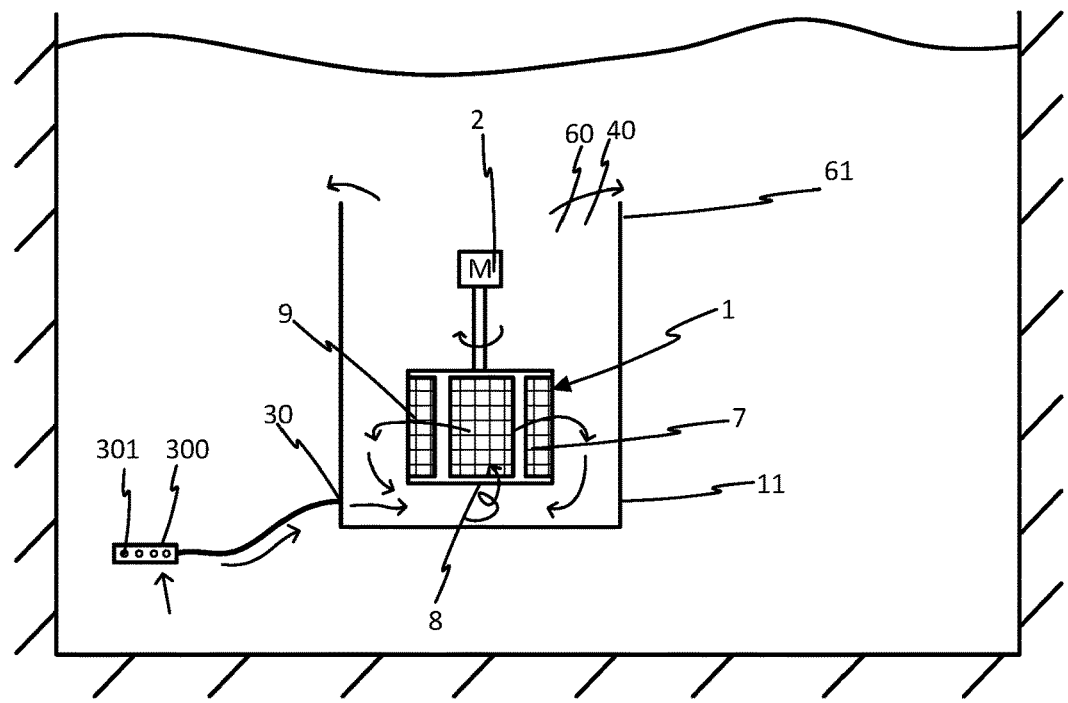

FIG. 6 discloses a second example of the operation of the reactor arrangement.

Figure 7:
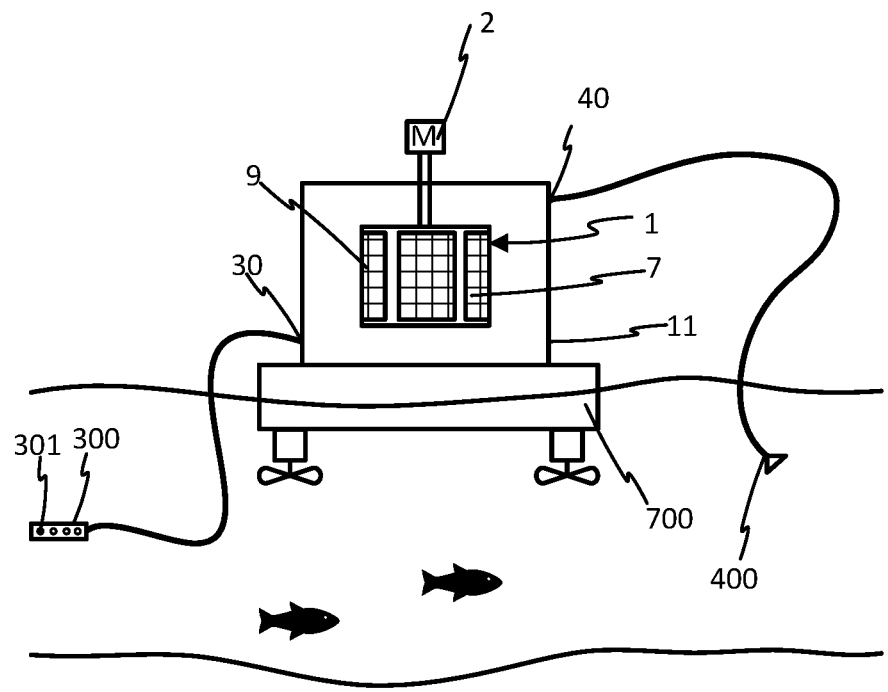

FIG. 7 discloses a third example of the operation of the reactor arrangement.

Figure 8:
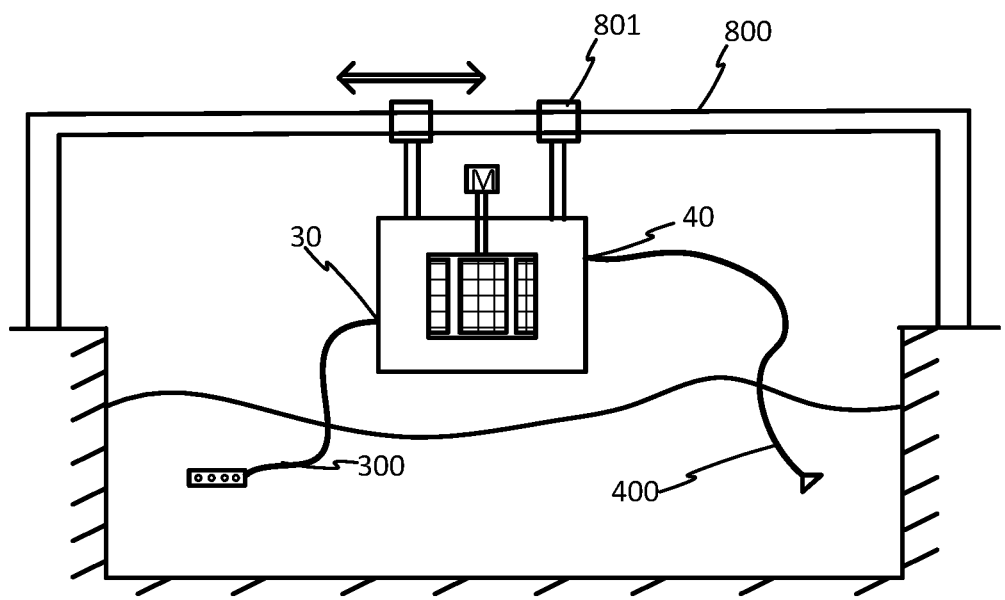

FIG. 8 discloses a fourth example of the operation of the reactor arrangement.

Figure 9:
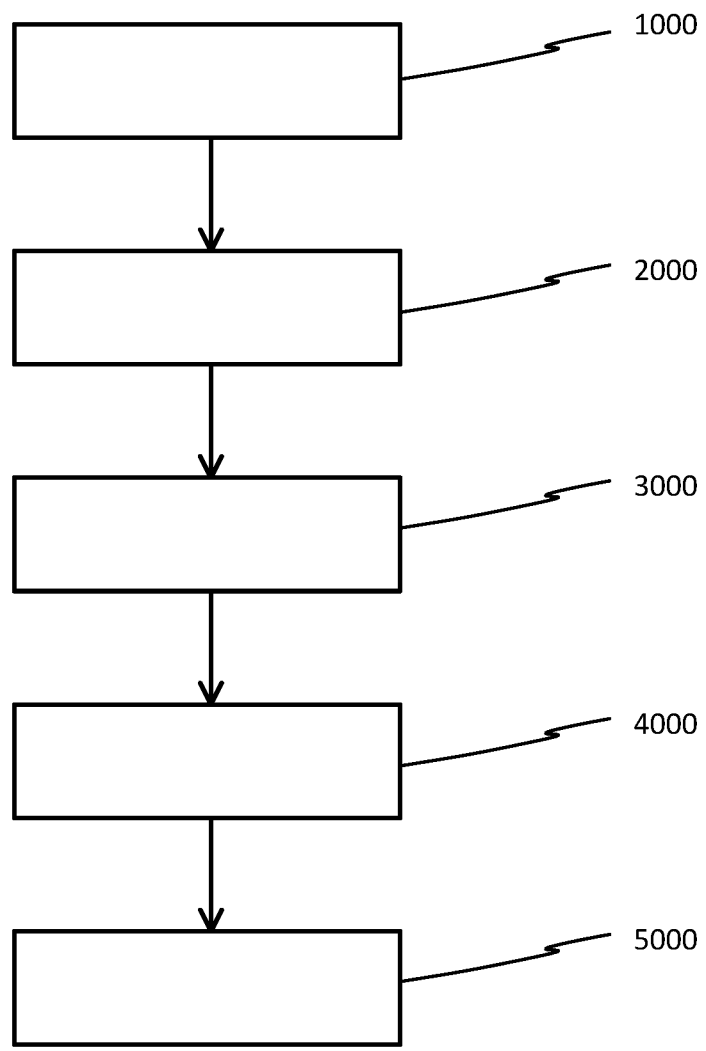

FIG. 9 is a flow chart of the method of operating the reactor arrangement in order to run a continuous process.

DETAILED DESCRIPTION OF PREFERRED EMBODIMENTS

In the following one embodiment of the present invention will be discussed starting with the overall design of a transformation device. FIG. 1 presents a side view of one embodiment of a transformation device 100. The transformation device 100 comprises a flow distributor 1 and a rotation and/or oscillation means 2, typically an electrically, pneumatically, or hydraulically driven motor, joined to the flow distributor 1 by a drive shaft 3. The flow distributor 1 has a top wall 4, a bottom wall 5 and a longitudinal peripheral wall 6 extending between the top wall 4 and the bottom wall 5. The walls 4, 5, 6 define a confinement 7.

The bottom wall 5 has a central opening 8 which is arranged in the vicinity of the centre of the bottom wall 5. The confinement 7 is allowed to communicate with the ambience via the opening 8. The cross-sectional area of the opening 8 is substantially smaller than the cross-sectional area of the bottom wall 5.

The flow distributor 1 has an essentially cylindrical shape and the longitudinal peripheral wall 6 has an essentially circular cross-section. The peripheral wall 6 comprises fluid medium outlets 9. It goes without saying that the number and pattern of the fluid medium outlets 9 may be changed within the scope of the invention. The fluid medium outlets 9 are covered by a peripheral retaining mesh 12. The peripheral retaining mesh 12 is permeable for a fluid medium but impermeable for solid reaction members. It is to be understood that the fluid medium outlets 9 instead of being formed by a retaining mesh may be formed by longitudinally extending gaps formed by a spirally wound wire making up the peripheral wall 6.

The confinement 7 is configured to be provided with at least one solid reaction member (not disclosed). The at least one solid reaction member may be loosely contained in the confinement 7 or be provided in one or more cassettes to be received in the confinement 7. It is to be understood that the type of reaction member is adapted to the type of chemical process to be performed. As a non-limiting example, in the event the reactor arrangement should be used to clean radioactive water, the at least one solid reaction member could be Cs-Treat. The invention should however not be limited to the type of reaction member used.

Now turning to FIG. 2, one example of a reactor 200 with an implemented flow distributor 1 is disclosed. The reactor 200 comprises a cylindrical reaction vessel 11 having a first end portion 17 forming a bottom wall 18, a second end portion 19, and a longitudinal cylindrical side wall 16 extending between the first and second end portions 17, 19. The second end portion 19 may, as disclosed, be provided with an optional lid 20 forming a closed top wall. The cylindrical reaction vessel 11 may with remained function be provided as an open vessel without any top wall.

The cylindrical reaction vessel 11 houses a transformation device 100 comprising a flow distributor 1 of the type previously discussed in view of FIG. 1. The flow distributor 1 is arranged to be operated by a motor 2. The flow distributor 1 is preferably arranged with its longitudinal centre axis L1 extending essentially coaxially with the longitudinal centre axis L2 of the vessel 11. It is however to be understood that other orientations are possible with remained function.

The disclosed cylindrical reaction vessel 11 comprises at least one inlet port 30 arranged in the vicinity of the bottom wall 18 and at least one outlet port 40 arranged in the vicinity of an upper end portion 19 of the cylindrical side wall 16. Only one inlet port 30 and one outlet port 40 is disclosed. The number of inlet ports 30 must not equal the number of outlet ports 40. Each inlet port 30 and each outlet port 40 may be provided with a respective valve 31, 41 allowing the flow through the respective ports 30, 40 to be controlled. The valves 31, 41 may be controlled by a control computer.

Each of the at least one inlet port 30 is connected to a fluid supply member 300. The fluid supply member 300 comprises at least one inlet opening 301 configured to supply a fluid to the cylindrical reaction vessel 11 via said at least one inlet port 30. The fluid supply member 300 and different embodiments thereof will be further described below.

Each of the at least one outlet port 40 is connected to a fluid distribution member 400. The fluid distribution member 400 comprises at least one outlet opening 401 configured to let out the fluid from the cylindrical reaction vessel 11 via the at least one outlet port 40. The fluid distribution member 400 will be further described below.

The cylindrical reactor vessel 11 may comprise at least one optional opening 50 which may be fitted with, by way of example a member 500 for remote exchange of transformation matter or for receiving a measurement probe. Non-exclusive examples of measurement probes are thermometric or photometric sensor probes and various electrodes for carrying out electrochemical measurements. The measurement probe may be connected to a control computer to allow an analysis and control of the conditions prevailing in the cylindrical reaction vessel 11 and hence the process. The skilled person will realize that one and the same control computer may be used to control the full reactor arrangement and its operation.

Now turning to FIGS. 3A-3C, three different embodiments of the fluid supply member 300 are disclosed. It is to be understood that the fluid supply member 300 may be arranged in a number of ways within the scope of the invention.

FIG. 3A discloses one embodiment where the fluid supply member 300A is formed as a portion 303 of an elongated hose 302 or tube comprising multiple inlet openings 301 arranged along at least a portion of its longitudinal extension. Said portion may by way of example be arranged adjacent the free end of the hose 302, i.e. opposite the end which during use is connected to the reaction vessel 11. It is to be understood that said portion 303 may be integral with the hose 302 or tube or be arranged as a fitting to be attached to the free end of the hose or tube. Such fitting may be attached by means of a suitable connector 304.

The multiple inlet openings 301 may be arranged as through going perforations allowing fluid to be sucked from the ambience into the interior of the hose 302 or tube. In case of a hose, it is preferred that the hose is flexible.

The end of the fluid supply member opposite the perforated portion 303 is configured to be connected to the inlet port 30 of the cylindrical reaction vessel 11. The fluid supply member 300A preferably has a length that allows the perforated portion to be arranged remote from the cylindrical reaction vessel 11 no matter if the vessel 11 is submerged or not.

FIG. 3B discloses a second embodiment where the fluid supply member 300B is formed as a grid 305 with an array of multiple inlet openings 301. In the disclosed embodiment, the grid 305 is illustrated as a quadrangular grid 305 formed by tube sections communicating with each other. The grid 305 may be either rigid or flexible. The grid 305 is connected to a supply pipe 306 configured to be connected to the inlet port 30 of the cylindrical reaction vessel 11.

The wall portion of the grid 305 comprises multiple inlet openings 301. The multiple inlet openings 301 may be arranged as through going perforations allowing fluid to be sucked from the ambience into the interior of the grid 305 and further to the cylindrical reaction vessel 11 via the common supply pipe 306. The common supply pipe 306 preferably has a length that allows the grid 305 to be arranged remote from the cylindrical reaction vessel 11 no matter if the vessel 11 is submerged or not. It is to be understood that the grid 305 may have other configurations than a quadrangular extension.

FIG. 3C discloses a third embodiment where the fluid supply member 300C comprises a plurality of arms 307 in the form of tubes or hoses branching from a common supply pipe 306. The arms 307 may be either rigid or flexible. The common supply pipe 306 is configured to be connected to the inlet port 30 of the cylindrical reaction vessel 111. The arms 307 may comprise multiple inlet openings 301 arranged along their longitudinal extensions. The multiple inlet openings 301 may be arranged as through going perforations allowing fluid to be sucked from the ambience into the interior of the arms 307 and further to the cylindrical reaction vessel 11 via the common supply pipe 306. The common supply pipe 306 preferably has a length that allows the fluid supply member 300C to be arranged remote from the cylindrical reaction vessel 11.

Now turning to FIG. 4, one embodiment of a fluid distribution member 400 is disclosed. The fluid distribution member 400 is configured as a flexible hose 402. One end of the hose 402 is configured to be connected to the at least one outlet port 40 of the cylindrical reaction vessel 11. The other end of the flexible hose 402 has an outlet opening 401 which allows the fluid distribution member 400 to communicate with the ambience via said outlet opening 401.

The outlet opening 401 may be provided with an optional distributor 403, such as a nozzle or one or more openings allowing a distributed flow.

The flexible hose 402 of the fluid distribution member 400 preferably has a length that allows its outlet opening 401 to be remotely arranged from the cylindrical reaction vessel and especially from the inlet openings 301 of the fluid supply member 300.

The embodiments of the fluid supply member disclosed in FIGS. 3A-3C may be used as a fluid distribution member 400. The at least one fluid inlet will then instead work as a fluid outlet.

In the following a first example of the operation of the reactor arrangement will be described with reference to FIG. 5. The reactor arrangement is disclosed as being submerged below surface level in a pool or a pond filled with a fluid to be processed. The reactor arrangement is of the same type as that disclosed with reference to FIG. 2.

The confinement 7 of the flow distributor 1 is configured filled with at least one solid reaction member selected in view of the chemical process to be performed. A fluid supply member 300 is connected to the inlet port 30 of the cylindrical reaction vessel 11. Further, a fluid distribution member 400 is connected to the outlet port 40 of the cylindrical reaction vessel 11. The at least one inlet opening 301 of the fluid supply member 300 is arranged on a remote distance from the at least one outlet opening 401 of the fluid distribution member 400.

The flow distributor 1 is set to rotate by operating the motor 2. The rotation speed is adapted to the size of the flow distributor 1. A typical speed is in the range of 100-1000 rpm. The invention should however not be limited to this speed. As a result of a high-speed rotation of the flow distributor 1 a vortex is created inside the cylindrical reaction vessel 11. This will create a pump action which sucks fluid from the pool or pond into the cylindrical reaction vessel 11 via the at least one inlet opening 301 in the fluid supply member 300. As the fluid level in the vessel 11 increases, the fluid will be sucked into the flow distributor 1 via its bottom opening 8 and into the confinement 7 where it will come in contact with and react with the at least one solid reaction member. The thus processed fluid will by the centrifugal action be forced in the radial direction and leave the flow distributor 1 via its at least one fluid permeable outlets 9. This circulating flow of processed fluid intermixed with new non-processed fluid will continue as long as the high-speed rotation of the flow distributor 1 is continued. As the process continues, the vessel 11 will be filled with fluid and the surplus fluid and hence processed fluid will be forced to leave the vessel and be released to the ambience in the pool or pond via the at least one outlet port 40 and the fluid distribution member 400 connected thereto.

As the processed fluid is continuously released from the vessel 11 it will form a virtual fluid volume VFV in the pool which initially has a virtual cross section VCS as seen in a horizontal plane. This virtual cross section VCS will act as a shielding in view of the underlying volume in the pool. Further, this virtual fluid volume VFV of processed fluid has a higher quality as compared to the surrounding fluid in the pool. It is to be understood that even though the dwell time in the cylindrical reaction vessel 11 should not be sufficient to reach a complete chemical reaction, the dwell time will be sufficient to at least have initiated a chemical reaction which as such will render the released processed fluid to be of a higher quality than the non-processed fluid that is sucked into the vessel 11. As given above, in the context of the invention, the term "higher quality" should be understood as that the processed fluid has undergone a certain degree of chemical reaction or purification, which reaction or purification as such must not be complete. Rather, the quality should be higher than the overall quality in the pond or pool. By way of example it can have a lower degree of radioactivity or a different pH. In the event of a lower degree of radioactivity, the virtual fluid volume VFV will act as a shielding in view of the underlying volume in the pool or pond.

It is to be understood that in the long run, a general dissolution will occur due to natural movements in the overall fluid volume in the pool or pond. In terms of the pool or pond containing a radioactive fluid, the released processed fluid will have a shielding effect as seen in the vertical direction which prevents radioactivity from spreading in the atmosphere. The reduced radioactivity in the air above surface level will allow an improved better working environment for personnel in the area around the pool. This applies also after dissolution of the virtual fluid volume VFV of processed fluid.

The fluid distributor 1 is configured to be rotated continuously to provide a continuous chemical reaction as long as the at least one solid reaction member exhibits a sufficient yield. When the yield is below a certain threshold, the rotation of the flow distributor 1 is stopped. The fluid distributor 1 may then be disposed and replaced by a new. Alternatively, the confinement may be provided with a new, fresh solid reaction member.

It is to be understood that the very same principle is applicable also to other environments such as water treatment in a pond of lake water in order of increasing or decreasing pH or when treating leachate in a pool.

Now turning to FIG. 6, a second embodiment is disclosed. The arrangement differs from that disclosed in FIG. 5 in that the cylindrical reaction vessel 11 has an open mouth 60 delimited by an upper edge 61 of the cylindrical reaction vessel 11. The open mouth 60 acts as an outlet port 40.

As the vessel 11 is filled with fluid during operation of the aggregate, the surplus fluid will leave the vessel 11 via the open mouth 60 in order to be distributed to the overall fluid volume in the pool or pond. This principle is applicable no matter if the vessel 11 is fully submerged, partially submerged or arranged above fluid level in the pool or pond. This type of vessel 11 is suitable to be used when it comes to processing of a fluid where there is no need to provide any shielding action.

Now turning to FIG. 7, a third embodiment is disclosed. The arrangement differs from that disclosed in FIG. 5 in that the cylindrical reaction vessel 11 is arranged on a floating platform 700. A fluid supply member 300 is connected to the inlet port 30 of the vessel 11. Further, a fluid distribution member 400 is connected to the outlet port 40 of the vessel 11. In the disclosed embodiment, both the fluid supply member 300 and the fluid distribution member 400 are submerged below surface level. It is to be understood that it is enough that at least the fluid supply member 300 is submerged.

The floating platform 700 may be a movable platform that may be anchored at a specific position in the pool or the pond. Alternatively, the floating platform 700 may be a remotely controlled vehicle or an autonomous vehicle. The floating platform may be connected to a GPS system.

Now turning to FIG. 8, a fourth embodiment is disclosed. The arrangement differs from that disclosed in FIG. 5 in that the cylindrical reaction vessel 11 is arranged above the fluid surface level in a pool supported by a scaffold 800. The scaffold 800 is provided as a traverse crane 801 allowing the vessel 11 to be moved across the pool. A fluid supply member 300 is connected to the inlet port 30 of the vessel 11. Further, a fluid distribution member 400 is connected to the outlet port 40 of the vessel 11. In the disclosed embodiment, both the fluid supply member 300 and the fluid distribution member 400 are submerged below surface level. It is to be understood that it is enough that at least the fluid supply member 300 is submerged.

The use of a scaffold 800 may be suitable in the event of a pool, since the area of a pool typically is defined by rigid side walls and thereby has a well-defined area. The scaffold may in such case be a permanent installation supported by the walls of the pool or be suspended in a ceiling above the pool.

Now turning to FIG. 9, the acts of a method for performing, by means of at least one solid reaction member(s), a biological or chemical transformation, or physical or chemical trapping from, or release of agents to, a fluidic media in a continuous process is schematically disclosed in a flow chart.

The method comprises the following acts:

Providing, 1000, a reactor arrangement of the type discussed above.

Adding, 2000, at least one solid reaction member to a confinement 7 of said flow distributor 1.

Submerging, 3000, the fluid supply member 300 and its at least one inlet opening 301 below the fluid surface level in a pool or in a pond, thereby allowing fluid to be supplied from the pool or pond to the cylindrical reaction vessel 11 via the at least one inlet opening 30.

Arranging, 4000, the cylindrical reaction vessel 11 with its at least one outlet port 40 at a position remote from the at least one inlet opening 301 of the fluid supply member 300, said remote position being arranged on a distance from the at least one inlet opening 301 so that any turbulence created in or around the at least one inlet opening 301 of the fluid supply member 300 during operation of the transformation device, does not influence the fluid in the area in and around the at least one outlet port 40 of the cylindrical reaction vessel 11.

Activating 5000 the means 2 for rotating and/or oscillating the transformation device 1, whereby the biological or chemical transformation, or physical or chemical trapping from, or release of agents to, the fluidic media is initiated and continuously run.

The person skilled in the art realizes that the present invention by no means is limited to the preferred embodiments described above. On the contrary, many modifications and variations are possible within the scope of the appended claims.

The solid reaction member has been described above as being configured to be contained inside the confinement 7 of the flow distributor 1. The reactor arrangement is equally applicable in the even the solid reaction members are configured to be provided as a suspension in the cylindrical reaction vessel 11. In order of preventing the solid reaction members from escaping the vessel 11, the inlet and outlet ports 30, 40 of the vessel 11 may be provided with a non-disclosed filter. As the flow distributor 1 is set to rotate at a high speed by the motor, the thus created vortex will cause the solid reaction members to be sucked and forced together with the fluid into the confinement 7 of the flow distributor 1 via its central bottom opening 8. The thus sucked solid reaction members will be trapped against the inner walls of the flow distributor 1 while the fluid is allowed to transfer in the radial direction out of the flow distributor 1 via the at least one fluid medium outlets 9 located in the peripheral wall 6 of the flow distributor 1. The solid reaction members are prevented from leaving the flow distributor 1 via the fluid medium outlets 9 by the peripheral retaining mesh 12.

The at least one reactor may further comprise an optional pump (not disclosed) configured to enhance the flow of fluid from the at least one inlet opening 301 of the fluid supply member 300, into the vessel 11 and out of the vessel 11 via the at least one outlet opening 401 of the fluid distribution member 400, thereby assisting inherent pumping action of the transformation device 100 during high-speed rotation and/or oscillating of the transformation device. The pump may be arranged in any suitable position between the different components of the arrangement.

To further enhance fluidic shear stress, the cylindrical reaction vessel 11 may comprise means for enhancing fluid shear stress 24. Said means are highly schematically disclosed as baffles. The baffles may be formed in a number of ways. By way of example, the inner wall 23 of the cylindrical reaction vessel 11 may comprise a pattern such as longitudinally extending undulations forming integrated baffles. As an alternative to using baffles integrated in the vessel, baffles may be provided as a removable scaffold to be inserted into the cylindrical reaction vessel 11. During normal operation of the flow distributor 1, the baffles contribute to enhancement of fluidic shear stress in any of the two rotary directions along the inner wall 23 of the vessel 11.

Additionally, variations to the disclosed embodiments can be understood and effected by the skilled person in practicing the claimed invention, from a study of the figures, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

The invention claimed is:

1. A reactor arrangement for performing, by means of at least one solid reaction member(s), a biological or chemical transformation, or physical or chemical trapping from, or release of agents to, a fluidic media in a continuous process, wherein said reactor arrangement comprises at least one reactor, wherein
said at least one reactor comprises a cylindrical reaction vessel within which at least one transformation device has been mounted for rotation and/or oscillation within the reaction vessel, said cylindrical reaction vessel comprising a bottom wall and a cylindrical side wall extending from the bottom wall; and
wherein said transformation device comprises:
a flow distributor having an essentially cylindrical shape configured to contain solid reaction members, a first essentially flat surface, a second essentially flat surface, and a peripheral wall having an essentially circular cross-section, at least one fluid medium inlet located in vicinity of the centre of said first and/or second surface, said inlet being adapted for receiving fluid medium and adapted for receiving initially suspended solid reaction members, at least one fluid medium outlet permeable for said fluid medium but impermeable for solid reaction members held within the peripheral wall, said outlet(s) being located on said peripheral wall, a driving shaft located on said first surface for enabling rotation or oscillation of the flow distributor, and at least one confinement wherein said solid reaction member(s) can be trapped and said transformation is performed; and
a means for rotating and/or oscillating the transformation device within the reaction vessel; and
wherein the said cylindrical reaction vessel comprises:
at least one inlet port arranged in the vicinity of the bottom wall and at least one outlet port arranged in the vicinity of an upper end portion of the cylindrical reaction vessel,
and wherein
each of the at least one inlet port is connected to a fluid supply member configured to be submerged below the fluid surface level in a pool or a pond, said fluid supply member having at least one inlet opening configured to continuously supply a fluid from the pool or the pond to the cylindrical reaction vessel via said at least one inlet port, and
each of the at least one outlet port is configured to continuously let out the fluid from the vessel to the pool or the pond via the at least one outlet port.

2. The reactor arrangement according to claim 1, wherein the fluid supply member is an elongated hose or tube comprising multiple inlet openings arranged along the longitudinal extension thereof, a grid with an array of hoses or tubes comprising multiple inlet openings, a combination of one or more of an elongated hose or tube or a grid, each of them comprising multiple inlet openings, or a plurality of arms in the form of tubes or hoses branching from a common supply pipe, said arms comprising multiple inlet openings arranged along their longitudinal extensions.

3. The reactor arrangement according to claim 1, wherein
the cylindrical reaction vessel, during operation of the transformation device, is configured to be arranged above the fluid surface level in a pool or in a pond supported by a scaffold or by a floating platform; or
the cylindrical reaction vessel, during operation of the transformation device, is configured to be submerged in a pool or in a pond, while the at least one inlet opening of the fluid supply member is arranged to be submerged below the fluid surface level in said pool or pond at a position remote from the at least one outlet port of the cylindrical reaction vessel.

4. The reactor arrangement according to claim 1, wherein the at least one outlet port is formed by
an open mouth of the cylindrical reaction vessel opposite the bottom wall; or
by at least one through going opening in the cylindrical side wall.

5. The reactor arrangement according to claim 4, wherein each of the at least one outlet ports is connected to a fluid distribution member having at least one outlet opening, and
wherein the fluid distribution member, during operation of the transformation device, is configured to be arranged above the fluid surface in a pool or in a pond; arranged floating on the fluid surface in a pool or in a pond; or is configured to be submerged below the fluid surface level in said pool or pond in a position remote from the cylindrical reaction vessel and/or from the at least one inlet opening of the fluid supply member.

6. The reactor arrangement according to claim 1, wherein the cylindrical reaction vessel further comprises a top wall formed as a removable lid, and wherein the at least one outlet port is arranged in said top wall.

7. The reactor arrangement according to claim 1, wherein an inner surface of the cylindrical reactor vessel comprises means for enhancing fluidic shear stress in any of two rotary directions of the transformation device.

8. The reactor arrangement according to claim 1, wherein the cylindrical reaction vessel further comprises at least one opening which optionally may be fitted with a member for remote exchange of transformation matter or for receiving a measurement probe.

9. A method for performing, by means of at least one solid reaction member(s), a biological or chemical transformation, or physical or chemical trapping from, or release of agents to, a fluidic media in a continuous process, wherein said reactor arrangement comprises at least one reactor, comprising the acts of:
   a) providing the reactor arrangement according to claim 1;
   b) adding at least one solid reaction member to a confinement of said flow distributor;
   c) submerging the fluid supply member and its at least one inlet opening below the fluid surface level in a pool or in a pond, thereby allowing fluid to be supplied from the pool or pond to the cylindrical reaction vessel via the at least one inlet opening;
   d) arranging the cylindrical reaction vessel with its at least one outlet port at a position remote from the at least one inlet opening of the fluid supply member, said remote position being arranged on a distance from the at least one inlet opening so that any turbulence created in or around the at least one inlet opening of the fluid supply member during operation of the transformation device, does not influence the fluid in the area in and around the at least one outlet port of the cylindrical reaction vessel; and
   e) activating the means for rotating and/or oscillating the transformation device, whereby the biological or chemical transformation, or physical or chemical trapping from, or release of agents to, the fluidic media is initiated and continuously run.

10. The method according to claim 9, wherein
   the cylindrical reaction vessel containing the transformation device is arranged above the fluid surface level in a pool or in a pond supported by a scaffold or by a floating platform; or wherein
   the cylindrical reaction vessel is arranged submerged in a pool or in a pond.

11. The method according to claim 9, wherein the at least one outlet port of the cylindrical reaction vessel is an open mouth of the vessel opposite the bottom wall, and wherein the fluid is continuously let out from the vessel to the pool or pond by flooding an edge portion of the vessel delimiting said open mouth during rotation or oscillation of the transformation device.

12. The method according to claim 9, wherein the at least one outlet port of the cylindrical reaction vessel is connected to a fluid distribution member having at least one outlet opening, and wherein the fluid is continuously let out from the vessel to the pool or pond via the at least one outlet opening of the fluid distribution member during rotation or oscillation of the transformation device.

13. The method according to claim 9, wherein the fluidic media is a radioactive fluid, sea water, lake water, leachate or greywater.

* * * * *